US00PP21186P2

(12) United States Plant Patent
Wood

(10) Patent No.: US PP21,186 P2
(45) Date of Patent: Aug. 10, 2010

(54) ***HYDRANGEA* PLANT NAMED 'HARBITS'**
(50) Latin Name: *Hydrangea macrophylla*
Varietal Denomination: Harbits

(75) Inventor: Timothy D. Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 68 days.

(21) Appl. No.: 12/315,161

(22) Filed: Nov. 28, 2008

(51) Int. Cl.
*A01H 5/00* (2006.01)

(52) U.S. Cl. ..... Plt./250
(58) Field of Classification Search ..... Plt./250
See application file for complete search history.

*Primary Examiner*—Wendy C. Haas
(74) *Attorney, Agent, or Firm*—C.A. Whealy

(57) ABSTRACT

A new and distinct cultivar of *Hydrangea* plant named 'Harbits' characterized by its upright and mounded plant habit; strong roots and stems; strong and dark green-colored leaves; and large lacecap-type inflorescences with white and red purple bi-colored flowers.

2 Drawing Sheets

Botanical designation: *Hydrangea macrophylla.*
Cultivar denomination: 'HARBITS'.

BACKGROUND OF THE INVENTION

The present invention relates to a new and distinct cultivar of *Hydrangea* plant, botanically known as *Hydrangea macrophylla* and hereinafter referred to by the name 'Harbits'.

The new *Hydrangea* plant is a product of a planned breeding program conducted by the Inventor in Grand Haven, Mich. The objective of the breeding program was to develop new *Hydrangeas* with attractive foliage and flower coloration.

The new *Hydrangea* plant originated from an open-pollination during the summer of 2004 of the *Hydrangea macrophylla* 'Harlequin', not patented, as the female, or seed parent and an unknown selection of *Hydrangea macrophylla*. The new *Hydrangea* plant was discovered and selected by the Inventor on May 1, 2005 as a flowering plant within the progeny of the stated open-pollination in a controlled outdoor nursery environment in Grand Haven, Mich.

Asexual reproduction of the new cultivar by softwood cuttings in Grand Haven, Mich. 2005 has shown that the unique features of this new *Hydrangea* plant are stable and reproduced true to type in successive generations of asexual reproduction.

SUMMARY OF THE INVENTION

Plants of the new *Hydrangea* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Harbits'. These characteristics in combination distinguish 'Harbits' as a new and distinct cultivar of *Hydrangea:*

1. Upright and mounded plant habit.
2. Strong roots and stems.
3. Strong and dark green-colored leaves.
4. Large lacecap-type inflorescences with white and red purple bi-colored flowers.

Plants of the new *Hydrangea* differ primarily from plants of the female parent, 'Harlequin', in inflorescence form as plants of the new *Hydrangea* have lacecap-type inflorescences whereas plants of 'Harlequin' have mophead-type inflorescences.

Plants of the new *Hydrangea* can be compared to plants of 'Shamrock', disclosed in U.S. Plant Pat. No. 16,223. Plants of the new *Hydrangea* differ primarily from plants of 'Shamrock' in the following characteristics:

1. Plants of the new *Hydrangea* have duller (less glossy) leaves than plants of 'Shamrock'.
2. Plants of the new *Hydrangea* and 'Shamrock' differ in flower color as plants of 'Shamrock' have pink to dark red-colored flowers.

BRIEF DESCRIPTION OF THE PHOTOGRAPHS

The accompanying colored photographs illustrate the unique appearance of the new cultivar, showing the colors as true as it is reasonably possible to obtain in colored reproductions of this type. Colors in the photographs may differ from the color values cited in the detailed botanical description which accurately describe the colors of the new *Hydrangea.*

The photograph on the first sheet comprises a side perspective view of a typical flowering plant of 'Harbits' grown in an outdoor nursery.

The photograph on the second sheet is a close-up view of typical inflorescences of 'Harbits'.

DETAILED BOTANICAL DESCRIPTION

Plants used in the aforementioned photographs and in the following description were grown in Grand Haven, Mich. in ground beds in an outdoor nursery and under conditions which closely approximate commercial production conditions. Plants of the new *Hydrangea* had been growing for three years when the photographs and description were taken during the summer. In the following description, color references are made to The Royal Horticultural Society Colour Chart, 1995 Edition, except where general terms of ordinary dictionary significance are used.

Botanical classification: *Hydrangea macrophylla* 'Harbits'.

Parentage:

*Female, or seed, parent.*—*Hydrangea macrophylla* 'Harlequin', not patented.

*Male, or pollen, parent.*—Unknown selection of *Hydrangea macrophylla,* not patented.

Propagation:

*Type cutting.*—By softwood cuttings.

*Time to initiate roots.*—About 15 days at temperatures of about 27° C.

*Time to produce a rooted young plant.*—About two months at temperatures of about 27° C.

*Root description.*—Fine to thick, fibrous.

*Rooting habit.*—Freely branching; dense.

Plant description:

*Form/growth habit.*—Perennial shrub. Upright and mounded plant habit; broadly inverted triangle. Strong lateral branches; vigorous growth habit.

*Plant height.*—About 75 cm.

*Plant diameter or area of spread.*—About 65 cm.

*Branching habit.*—When pinched, freely branching with about 14 lateral branches per plant.

*Lateral branches.*—Length: About 36 cm. Diameter: About 6 mm. Internode length: About 7.5 cm. Texture: Smooth, glabrous. Strength: Strong. Color, young: Close to 144A. Color, older: Close to 198B.

Foliage description:

*Arrangement.*—Opposite, simple.

*Length.*—About 12.4 cm.

*Width.*—About 6.7 cm.

*Shape.*—Oblanceolate.

*Apex.*—Acuminate.

*Base.*—Cuneate.

*Margin.*—Serrate.

*Texture, upper and lower surfaces.*—Smooth; glabrous.

*Venation pattern.*—Pinnate.

*Color.*—Developing leaves, upper surface: Close to 141A. Developing leaves, lower surface: Close to 141B. Fully expanded leaves, upper surface: Close to 137A; venation, close to 139C. Fully expanded leaves, lower surface: Close to 137B; venation, close to 139C.

*Petiole.*—Length: About 4.1 cm. Diameter: About 4 mm. Texture, upper and lower surfaces: Smooth, glabrous. Color, upper and lower surfaces: Close to 139C.

Flower description:

*Flower type and habit.*—Single sterile and fertile flowers arranged on terminal lacecap-type panicles. Flowers face upright or outward.

*Fragrance.*—Very faint, pleasant.

*Natural flowering season.*—Continuous flowering from June to August in Grand Haven, Mich. Plants begin flowering about two months after pinching.

*Flower longevity, fertile flowers.*—Flowers last about two weeks on the plant and about two weeks as a cut flower; flowers not persistent.

*Flower longevity, sterile flowers.*—Flowers last about five months on the plant and about two weeks as a cut flower; flowers persistent.

*Quantity of flowers.*—Freely flowering; about 79 fertile flowers and about 12 sterile flowers per panicle.

*Panicle height.*—About 7 cm.

*Panicle diameter.*—About 15 cm.

*Flower diameter, fertile flowers.*—About 1.1 cm.

*Flower depth (height), fertile flowers.*—About 1.1 cm.

*Flower diameter, sterile flowers.*—About 5 cm.

*Flower depth (height), sterile flowers.*—About 4 mm.

*Flower buds, fertile and sterile flowers.*—Length: About 4 mm. Diameter: About 4 mm. Shape: Obovate to rounded. Color: Close to 62B.

*Petals, fertile flowers only.*—Arrangement: Four to five in a single whorl. Length: About 5 mm. Width: About 3 mm. Shape: Lanceolate, cupped. Apex: Acute. Base: Attenuate. Margin: Entire. Texture, upper and lower surfaces: Smooth, glabrous. Color: When opening and fully opened, upper surface: Close to 66B. When opening and fully opened, lower surface: Close to 66B.

*Sepals, fertile flowers.*—Quantity per flower: Six in a single whorl. Length: About 0.5 mm. Width: About 1 mm. Shape: Roughly deltoid. Apex: Acute. Base: Truncate. Margin: Entire. Texture, upper and lower surfaces: Smooth, glabrous. Color: When opening, upper and lower surfaces: Close to 66D. Fully opened, upper and lower surfaces: Close to 66D.

*Sepals, sterile flowers.*—Quantity per flower: Four in a single whorl. Length: About 3 cm. Width: About 2.5 cm. Shape: Spatulate. Apex: Obtuse and retuse. Base: Attenuate. Margin: Entire. Texture, upper and lower surfaces: Smooth, glabrous. Color: When opening, upper and lower surfaces: Close to 145D. Fully opened, upper surface: Close to 66D; towards the margins, close to 155D. Fully opened, lower surface: Close to 73D.

*Peduncles, fertile and sterile flowers.*—Angle: Erect to about 20° from vertical. Strength: Strong. Length: About 1.9 cm. Diameter: About 3 mm. Texture: Smooth, glabrous. Color: Close to 144A.

*Pedicels, fertile flowers.*—Angle: Erect to about 15° from vertical. Strength: Moderately strong. Length: About 6 mm. Diameter: About 1 mm. Texture: Smooth, glabrous. Color: Close to 66C.

*Pedicels, sterile flowers.*—Angle: About 15° from vertical. Strength: Strong. Length: About 2.5 cm. Diameter: About 2 mm. Texture: Smooth, glabrous. Color: Close to 66D.

*Reproductive organs, fertile flowers only.*—Stamens: Quantity per flower: About ten. Anther size: About 1 mm by 0.5 mm. Anther shape: Oblong. Anther and stamen color: Close to 78A. Pollen amount: Scarce to moderate. Pollen color: Close to 202D. Pistils: Pistil quantity per flower: About four. Pistil length: About 2 mm. Stigma shape: Rounded. Stigma color: Close to 78A. Style length: About 1 mm. Style color: Close to 78A. Ovary color: Close to 66C.

*Seeds.*—Quantity per inflorescence: Numerous; dust-like. Size: Less than 0.1 mm by less than 0.1 mm. Color: Close to 200D.

Disease/pest resistance: Plants of the new *Hydrangea* have been observed to have good resistance to Powdery Mildew. Plants of the new *Hydrangea* have not been observed to be resistant to pests or other pathogens common to *Hydrangea.*

Temperature tolerance: Plants of the new *Hydrangea* have been shown to be tolerant to temperatures ranging from about −27° C. to about 37° C.

It is claimed:

1. A new and distinct *Hydrangea* plant named 'Harbits' as illustrated and described.

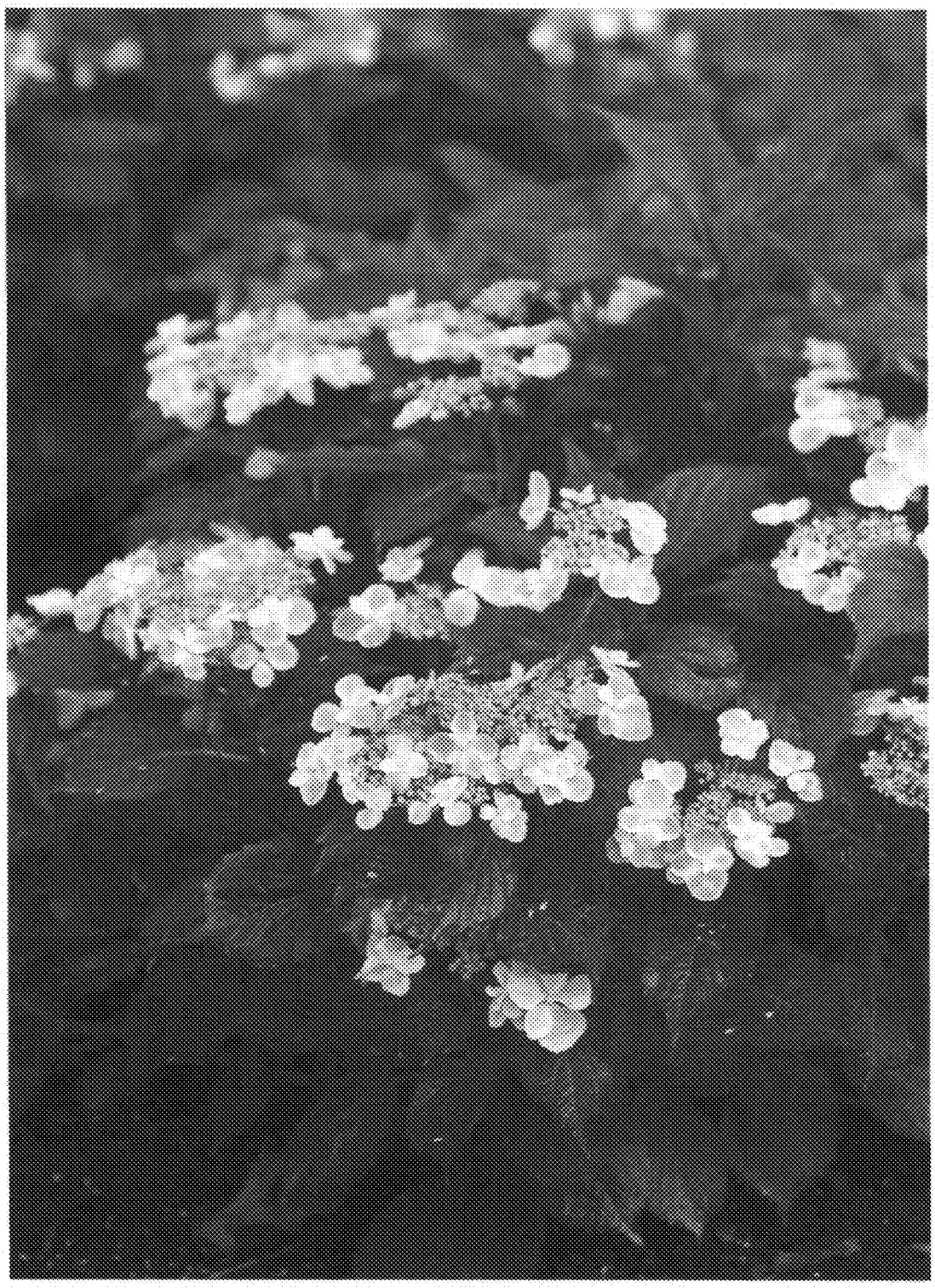

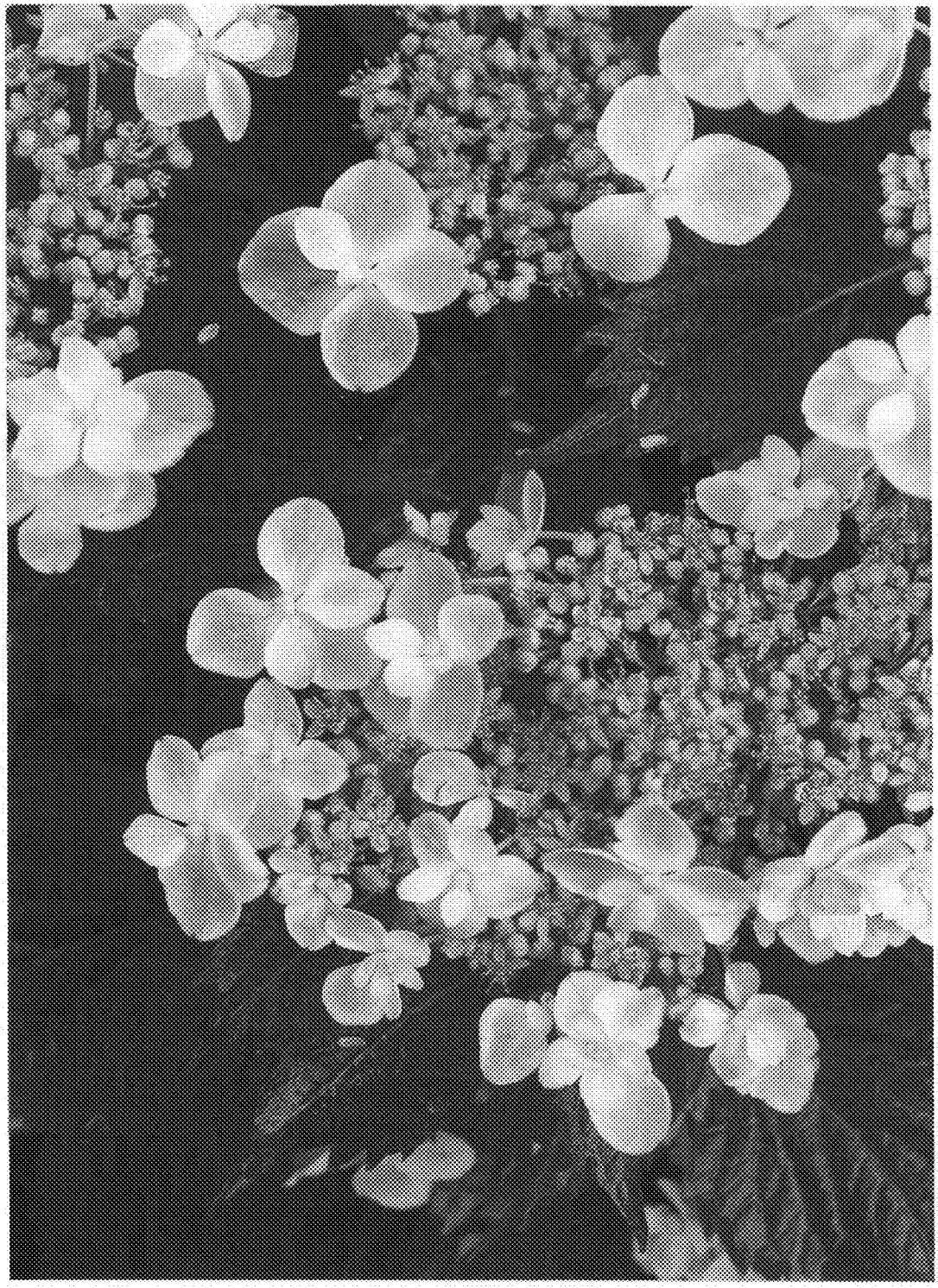

* * * * *